United States Patent [19]

Hanes

[11] Patent Number: 4,831,183
[45] Date of Patent: May 16, 1989

[54] CONJUGATED ALKADIENE TELOMERIZATION TO ORGANOOXYALKADIENES

[75] Inventor: Ronnie M. Hanes, Milford, Ohio

[73] Assignee: National Distillers and Chemical Corporation, New York, N.Y.

[21] Appl. No.: 259,475

[22] Filed: Oct. 17, 1988

Related U.S. Application Data

[63] Continuation of Ser. No. 23,741, Mar. 9, 1987, abandoned, which is a continuation-in-part of Ser. No. 773,718, Sep. 9, 1985, abandoned.

[51] Int. Cl.$^4$ ............................................. C07C 41/06
[52] U.S. Cl. .................................... 568/690; 568/579; 568/630; 568/657; 568/655; 568/663; 568/686
[58] Field of Search ............... 568/690, 597, 630, 657, 568/655, 663, 686

[56] References Cited

U.S. PATENT DOCUMENTS 3,670,032  6/1972  Romanelli .
3,769,352 10/1973  Romanelli .
4,142,060  2/1979  Kuntz .

FOREIGN PATENT DOCUMENTS 1248593 10/1971 United Kingdom .
2074156 10/1981 United Kingdom .

Primary Examiner—Howard T. Mars
Attorney, Agent, or Firm—Kenneth D. Tremain

[57] ABSTRACT

A process for the telomerization of a conjugated alkadiene with an organic hydroxy compound to produce an organo-oxyalkadiene is disclosed. A palladium catalyst having an ionic ligand is employed in a substantially oxygen-free environment in the presence of an aprotic polar solvent so that the reaction products may be separated from the catalyst by solvent extraction with a hydrocarbon solvent.

20 Claims, No Drawings

CONJUGATED ALKADIENE TELOMERIZATION TO ORGANOOXYALKADIENES

This is a continuation of application Ser. No. 023,741, filed Mar. 9, 1987 which is a continuation-in-part of U.S. patent application, Ser. No. 773,718 filed Sept. 9, 1985, both now abandoned.

BACKGROUND OF THE DISCLOSURE

1. Field of the Invention

The invention is directed to the telomerization of a conjugated alkadiene with organic hydroxy compounds in the presence of a catalyst to produce an organo-oxyalkadiene.

2. Background of the Prior Art

The telomerization of conjugated alkadienes with alkanols by means of palladium catalysts is a convenient route for the preparation of alkoxy alkadienes such as the reaction of butadiene with methanol to produce 8-methoxy-1,6-octadiene. Because of the high cost of palladium catalyst, any industrial process employing catalysts of this type requires recycling of the catalyst in order to minimize the cost of production. Accordingly, catalyst recovery and recycle is of primary concern along with selectivity, yields and speed of reaction in the selection of a catalyst for telomerization reactions of this type. Although palladium type catalysts are effective in promoting these types of telomerization reactions, after recovering and recycling the catalyst for subsequent reactions, it has been observed that the activity of the catalyst drops off significantly. Additionally, prior to recovering and recycling the catalyst, the various products of the telomerization reaction must be separated by a process which does not substantially damage or deactivate the catalyst or cause a loss of the catalyst. The prior art method of recovering the telomerization product generally comprised distillation of the reaction product to remove them from the catalyst and resulted in catalyst loss and/or deactivation.

Typical of the prior art processes involving the reaction of conjugated alkadienes with alkanols in the presence of a palladium catalyst are U.S. Pat. Nos. 3,670,032 and 3,769,352 both issued to Romanelli. The process of these patents utilize a zero valence palladium catalyst including a non-ionic ligand. Such a catalyst system is soluble in non-polar organic solvents, such as hydrocarbons, as is the unsaturated alcohol or ether product. The problem with the use of these catalysts lies in the separation of the catalyst from the product. Such separation occurs by distillation. As stated above, this separation is characterized by catalyst deactivation and/or loss.

An attempt to overcome the difficulties occasioned by the use of non-ionic ligands is illustrated by U.S. Pat. No. 4,142,060 issued to Kuntz. In Kuntz the palladium catalyst system employs an ionic ligand which is soluble in the protic polar solvent used therein, water. As such, the catalyst is almost completely separated from the diene product by phase separation. However, this solution creates other difficulties. If, as Kuntz proposes in one preferred embodiment, water is added as solvent before or during the reaction, the preferential solubility of the palladium catalyst system in water, while the reactants are in the non-polar organic phase, leads to low rate of reaction due to poor contact between the reactants and the catalyst. If, on the other hand, water is added after the reaction is complete, a new problem, the separation of the catalyst from the water, arises. Such a problem is very similar to the difficulty of separating the catalyst from the non-polar solvent encountered in art exemplified by the Romanelli patents. Of course, if no attempt to separate the catalyst from the water is made, then upon recycle the problem recited above, directed to the case where addition of water occurs before the reaction, ensues. Upon recycle the rate of reaction decreases because of the separation of the catalyst, in the polar phase, from the reactants, in the non-polar organic phase.

Even if the Kuntz disclosure employs a miscibilizing solvent to overcome the problem of catalyst-reactant separation during the reaction a new problem is presented. The miscibilizing solvent must be removed by distillation. This additional operation adds a difficult complication to the telomerization process.

Accordingly, it is an object of the present invention to overcome these and other difficulties encountered in the prior art.

It is a further object of the present invention to provide a method for the telomerization of a conjugated alkadiene with an organic hydroxy compound to produce an organo-oxyalkadiene.

It is also an object of the invention to provide a process for conducting the aforesaid telomerization reaction by means of a palladium-type catalyst and which process provides a novel method for separating the organooxyalkadiene from the catalyst so that the catalyst can be recycled without substantial catalyst loss or substantial loss of catalyst activity.

SUMMARY OF THE INVENTION

These and other objects have been achieved according to the present invention which comprises a method for the telomerization of a conjugated alkadiene with an organic hydroxy compound to produce an organo-oxyalkadiene by reacting the aforesaid alkadiene and hydroxy compound with a palladium catalyst having a phosphine, arsine or stibene ligand in which the ligand also contains a hydrophylic group. It is essential that the process is conducted substantially in the absence of oxygen and in the presence of a solvent for the catalyst, such solvent being an aprotic polar organic solvent, so that the reaction products may be separated from the solution of the catalyst by extraction with a solvent such as a hydrocarbon that is substantially immiscible in the aprotic polar solvent and which acts as a solvent for the reaction products. By employing the method of the present invention deactivation of the catalyst during the telomerization reaction is avoided by substantially eliminating contact of the reaction mass with oxygen and further, by using a solvent extraction process that minimizes exposure of the reaction products and the catalyst to air, catalyst deactivation is further minimized. Lastly, by employing a solvent extraction method for separating reaction products from the catalyst, deactivation and/or loss of catalyst by distillation is avoided.

DETAILED DESCRIPTION OF THE INVENTION

The present invention broadly relates to a method for the telomerization of a conjugated alkadiene with an organic hydroxy compound to produce an organo-oxyalkadiene comprising reacting said conjugated alkadiene with said hydroxy compound in the presence of a catalytically effective amount of a catalyst compound comprising:

$$[PdR^1{}_2] [R^2{}_xY(R^3Z)_y] \quad (I).$$

$R^1$ is any anionic group displaced by the organic hydroxy compound except a halide. $R^1$ especially comprises an organo acyclic or cyclic carboxylate group having from 1 to about 10 carbon atoms, especially an acetate group. $R^1$, more particularly, may comprise a straight chain, branched chain or cyclic ester having from 1 to about 10 carbon atoms and is especially an ester containing a phenyl radical or a lower alkyl radical having from 1 to about 4 carbon atoms.

The palladium component of the catalyst complex, $[PdR^1{}_2]$ herein can also be zero-valent palladium, a palladium-containing composition which will provide zero valent palladium, i.e., will undergo reduction, under the conditions of the reaction and/or a palladium (II) salt, with or without the additional presence of a reducing agent such as an alkali metal alkoxide, alkali metal acetate and/or alkali metal borohydride. Among such palladium-containing compositions are palladium (II) acetate, palladium (II) formate, palladium (II) octanoate, palladium (II) propionate, palladium (II) nitrate, palladium (II) bis ($\pi$-allyl), palladium sulfate and the like.

In the above formula (I) the ligand $$[R^2{}_xY(R^3Z)_y]$$

comprises compounds wherein:

(a) $R^2$ is a hydrocarbyl group, such as phenyl, benzyl, naphthyl or a cyclic or acyclic aliphatic hydrocarbon having up to about 10 carbon atoms;

(b) Y is phosphorus, antimony, arsenic or nitrogen;

(c) x and y are integers whose total is the valence of Y with the proviso that y is not zero;

(d) $R^3$ is a hydrocarbyl group, such as a cyclic or acyclic hydrocarbon, having up to about 6 carbon atoms such as phenyl, ethylene, benzyl or naphthyl;

(e) Z is an ionic group selected from the group consisting of $-SO_3M$, $-COOM$ and a quaternary ammonium group. An example of an ammonium group is $N^+R^4{}_3A^-$ (f) M is an alkali metal or an ammonium ion;

(g) $R^4$ is $C_1-C_6$ alkyl, benzyl or mixtures thereof; and (h) $A^-$ is an anion such as nitrate, chloride or sulfate.

Ligands which are especially suitable comprise: Tris-(p-carboxyphenyl)phosphine, trisodium salt,

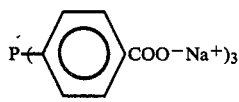

Bis-(p-carboxyphenyl)phenylphosphine, disodium salt,

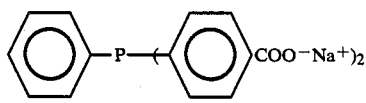

p-Carboxyphenyldiphenylphosphine, sodium salt

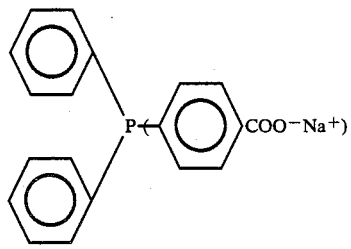

Tris-(p-trimethylammoniophenyl)phosphine trichloride,

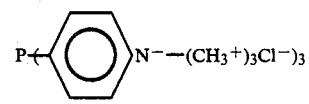

Bis-(p-trimethylammoniophenyl)phenylphosphine dichloride,

p-Trimethylammoniphenyl diphenylphosphine chloride,

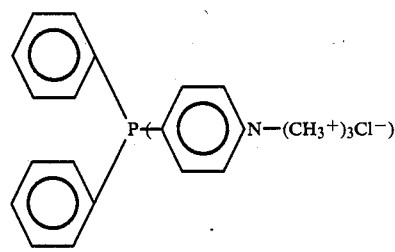

Sodium diphenylphosphinobenzene-m-sulfate,

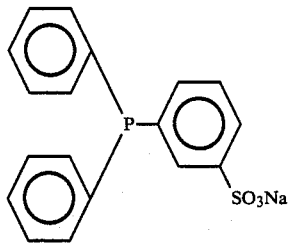

Trisodium-tris(m-sulfophenyl)phosphine,

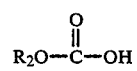

Trisodium-tris(m-sulfophenyl)arsine,

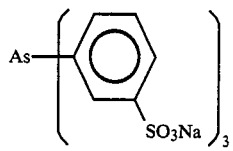

The various arsine and stibine homologs of the foregoing ligands may also be employed. The ratio of ligand to palladium is from about 2:1 to about 50:1 on a molar basis. The ligand component is added to the catalyst in subsequent telomerization reactions because of loss due to oxidation, product separation and the like.

In another aspect of the invention, it has been discovered that the molar ratio of the alkadiene to the organic hydroxy compound influences the yield and selectivity of the reaction and that an excess of the organic hydroxy compound is required to maximize such yields and selectivities. By an excess is meant that the organic hydroxy compound is present in more than a stoichiometric amount (i.e., greater than one mole of organic hydroxy compound to two moles of conjugated alkadiene). The molar ratio of the aforesaid hydroxy compound to the aforesaid alkadiene is from about 0.6:1 to about 3:1 and preferably from 0.75:1 to about 2.5:1.

The organic hydroxy compound used in the telomerization reaction of the present invention is a compound having the formula ROH where R is $C_1$–$C_4$ alkyl, $C_5$–$C_6$ cycloalkyl or phenyl. Organic hydroxy compounds within the contemplation of the present invention include methanol, ethanol, 1-propanol, 2-propanol, 2-butanol, phenol, hydroxycyclohexane, hydroxycyclopentane and the like.

The conjugated alkadiene has anywhere from 4 to about 6 carbon atoms and comprises butadiene, isoprene, chloroprene, piperylene, 1,3-pentadiene and the like.

An essential aspect of the process of the present invention is the employment of a solvent for the catalyst which is an aprotic polar solvent. An aprotic polar solvent is an organic compound characterized by the absence of an active proton.

Aprotic solvents within the contemplation of the instant invention include sulfolane and N-substituted amides in which the hydrogen attached to the amide nitrogen is substituted by a hydrocarbyl group, e.g., 1-methylpyrolidin-2-one, N,N-dimethylacetamide, N,N-diethylacetamide, N,N-dimethylformamide, N-methylpiperidone, 1,5-dimethylpyrrolidin-2-one, 1-benzylpyrrolidin-2-one, N,N-dimethylpropionamide, hexamethylenephosphoric triamide and the like. The amides within the scope of this invention are all liquid at ambient temperature. The most preferred aprotic solvents contemplated for use in the present invention are N,N-dimethylformamide (DMF) and sulfolane.

The use of an aprotic polar solvent facilitates extraction of the product and recovery and recycling of the catalyst. In the present process, it is possible to extract the telomer product from the reaction mixture by using a hydrocarbon, such as hexane, which is a solvent for the telomer. Any similar hydrocarbon solvent may also be employed. For example, an alkane of about 5 to about 10 carbon atoms, such as n-pentane, n-hexane, n-heptane, n-octane, iso-octane, n-nonane, cyclohexane, methylcyclohexane, mixtures thereof and the like may be used. In general, the hydrocarbon solvents comprise any acyclic or cyclic saturated hydrocarbon having up to about 10 carbon atoms. Where the hydrocarbons are gaseous at room temperature, the separation is conducted at elevated pressures at temperatures less than the critical temperature of the hydrocarbon. Hexane is a particularly preferred organic solvent for extraction of the telomer.

The extraction of the product leaves the catalyst in the aprotic polar solvent for recycling and thus avoids exposing the catalyst to fractional distillation processes typically used for product-catalyst separation. Multiple extractions can be used in those cases where the telomer is soluble to some extent in the polar solvent. Cocurrent or countercurrent extraction processes are also utilized in the separation of the catalyst and the telomer. The aprotic polar and the hydrocarbon solvents are employed in combination with one another as noted above and are selected so as to form an immiscible pair. This combination is within the ordinary skill of the art.

The reaction may be conducted at pressures from atmospheric pressure up to about 200 psig and at temperatures from about 60° C. to about 80° C. and especially from about 65° C. to about 75° C.

The following examples are illustrative:

EXAMPLE 1

Butadiene Telomerization with Methanol

To a pyrex tube were added 0.0099 g (0.045 mmoles) palladium acetate, 0.049 g. (0.134 mmoles) sodium diphenylphosphinobenzene-m-sulfonate, 8 ml. methanol and 8 ml. butadiene. The tube was sealed and placed in a 75° C. oil bath for 1.5 hours. Very little butadiene gas remained in the tube and a bright yellow solution with no precipitate was recovered. The product was analyzed by glc on a silar 10C column and contained 5.6 g. (40 mmoles) of methoxyoctadiene.

EXAMPLE 2

Butadiene Telomerization with Methanol, Recycle of Catalyst

To a pyrex tube was added 0.0103 g. palladium acetate, 0.0500 g. of the same ligand employed in Example 1, 8 ml. methanol, 5 ml. sulfolane and 10 ml. butadiene. The tube was sealed and placed in a 70° C. oil bath for 1 hour. The tube was cooled, vented and a sample taken for glc analysis. The remainder was extracted with 25 ml. hexane and the sulfolane layer returned to the tube with 8 ml. methanol and 10 ml. butadiene was added. The tube was placed in a 70° C. oil bath for 1.5 hours. The product solution was extracted twice with 25 ml. hexane, then 8 ml. methanol and 10 ml. butadiene were added to the sulfolane layer and the tube placed in a 70° C. oil bath for 1.5 hours. The product obtained after each one of the telomerizations was analyzed in the same manner as set forth in Example 1 and each contained 7.5 g, or 50 mmoles, methoxyoctadiene.

EXAMPLE 3

Butadiene Telomerization

To a pyrex tube was added 0.0202 g. palladium acetate, 0.1033 g. of the ligand employed in Example 1, 16 ml. methanol, 10 ml. sulfolane and 20 ml. butadiene. The tube was sealed and placed in a 70° C. oil bath for 1.5 hours. The product solution was extracted twice with 25 ml. portions of hexane. To the sulfolane layer was added 16 ml. methanol and 20 ml. butadiene. The tube was sealed and placed in a 70° C. oil bath for two hours.

The product solution (55 ml.) was extracted twice with 75 ml. portions of hexane. To the sulfolane layer was added 8 ml. methanol and 20 ml. butadiene. The tube was returned to a 75° C. oil bath for two hours. The product solution was extracted with 75 ml. hexane and the sulfolane layer analyzed by atomic absorption and 0.068 grams Pd (75% of original) was found.

Hexane was removed from the telomer extracted in each run and the residue was weighed. In the first run 1.5 g. was recovered, in the second 14.9 g. and in the third 17.5 g. These residues were analyzed and were found to contain 29.0 g. (207 mmoles) methoxyoctadiene.

EXAMPLE 4

Butadiene Telomerization with Methanol

To a pyrex tube were added 0.206 gms palladium acetate, 0.1030 gms of the ligand employed in Example 1, 16 ml. methanol, 10 ml. DMF and 20 ml. butadiene. The tube was placed in a 70° C. oil bath for two hours. The product solution was extracted twice with 75 ml. hexane. The DMF solution was returned to the tube with 8 ml. methanol and 20 ml. butadiene. The tube was placed in a 70° C. oil bath for 2 hours and the product solution extracted twice with 75 ml. of hexane in each extraction. The telomer obtained was analyzed by glc in the same manner as in Example 1 and contained 28 grams (200 mmoles) methoxyoctadiene.

The telomers obtained according to the method of the invention may be carbonylated to form unsaturated esters by art known methods. The esters obtained may be hydrogenated and used as lubricants, plasticizers or functional fluids or may be hydrolyzed to form an acid having unsaturated groups. The acid obtained may be incorporated into polyesters manufactured from phthalic anhydride, glycols and maleic anhydride which are subsequently cross-linked with styrene, all of which is known in the art. The unsaturated acid obtained provides a site along the polyester chain for cross-linking with styrene or equivalent monomers.

Although the invention has been described by reference to certain embodiments, it is not intended that the novel method for the telomerization of butadiene and the separation of the telomer be limited thereby but that modifications are intended to be included as falling within the broad scope and spirit of the foregoing disclosure and the following claims.

What is claimed is:

1. A method for the telomerization of a conjugated alkadiene consisting essentially of reacting a mixture consisting essentially of a conjugated alkadiene with an organic hydroxy compound having the formula ROH where R is $C_1$-$C_4$ alkyl, $C_5$-$C_6$ cycloalkyl or phenyl in the presence of a catalytically effective amount of a catalyst compound having the structural formula

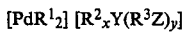

where $R^1$ is any anionic group displaced by the organic hydroxy compound with the proviso that $R^1$ is not a halide; $R^2$ is a hydrocarbyl group having up to about 10 carbon atoms; Y is phosphorus, antimony, arsenic or nitrogen; $R^3$ is a hydrocarbyl group having up to about 6 carbon atoms; Z is an ionic group selected from the group consisting of —$SO_3M$, —COOM and a quaternary ammonium; x and y are integers, with the proviso that y is not zero, whose sum is equal to the valence of Y; and M is alkali metal or quaternary ammonium, in the presence of an aprotic polar solvent, said reaction conducted in the substantial absence of oxygen, whereby a telomer is obtained; and extracting said telomer with a hydrocarbon solvent.

2. The method of claim 1 where said conjugated alkadiene has from about 4 to about 6 carbon atoms.

3. The method of claim 1 where said conjugated alkadiene is selected from butadiene, isoprene, chloroprene, piperylene and 1,3-pentadiene.

4. The method of claim 1 wherein said organic hydroxy compound is selected from the group consisting of methanol, ethanol, 1-propanol and 2-propanol.

5. The method of claim 4 where said organic hydroxy compound is methanol.

6. The method of claim 1 where $R^1$ is an organo carboxylate group; $R^2$ is phenyl, benzyl or a cyclic or acyclic aliphatic hydrocarbon having from 1 to about 10 carbon atoms; and $R^3$ is ethylene, phenyl, benzyl or naphthyl.

7. The method of claim 6 where $R^1$ is a lower alkyl ester group; and $R^2$ is a cyclic or acyclic aliphatic group.

8. The method of claim 1 where Z is —$NR^4_3A$ wherein $R^4$ is $C_1$-$C_6$ alkyl, benzyl or mixtures thereof; and A is a nitrate, chloride or sulfate anion.

9. The method of claim 1 where Z is —$SO_3M$.

10. The method of claim 1 where said reaction is conducted at a temperature of from about 60° to about 80° C. at atmospheric pressure up to about 200 psig.

11. The method of claim 1 where said aprotic polar solvent is selected from N-substituted amides and sulfolane.

12. The method of claim 11 where said aprotic polar solvent is N,N-dimethylformamide.

13. The method of claim 11 where said aprotic polar solvent is sulfolane.

14. The method of claim 1 wherein said hydrocarbon solvent is a saturated cyclic or acyclic hydrocarbon containing 1 to about 10 carbon atoms.

15. The method of claim 14 where said hydrocarbon solvent is an aliphatic hydrocarbon that is liquid at room temperature.

16. The method of claim 15 wherein said aliphatic hydrocarbon is an alkane of about 5 to 10 carbon atoms.

17. The method of claim 16 wherein said alkane is n-hexane.

18. The method of claim 1 wherein said hydroxy compound and said alkadiene are present in said telomerization method such that the molar ratio of said hydroxy compound to said alkadiene is in the range of between abot 0.6:1 and about 3:1.

19. The method of claim 18 wherein said molar ratio of said hydroxy compound to said alkadiene is in the range of between about 0.75:1 and about 2.5:1.

20. The method of claim 5 wherein said conjugated alkadiene is butadiene.

* * * * *